US012201471B2

(12) United States Patent
Torjesen et al.

(10) Patent No.: US 12,201,471 B2
(45) Date of Patent: Jan. 21, 2025

(54) PASSIVE-ULTRASOUND-SENSOR-BASED INITIALIZATION FOR IMAGE-BASED DEVICE SEGMENTATION

(71) Applicant: KONINKLIJKE PHILIPS N.V., Eindhoven (NL)

(72) Inventors: Alyssa Torjesen, Charlestown, MA (US); Kunal Vaidya, Boston, MA (US); Sibo Li, Waltham, MA (US); Molly Lara Flexman, Melrose, MA (US); Ameet Kumar Jain, Boston, MA (US); Alvin Chen, Cambridge, MA (US); Ramon Quido Erkamp, Swampscott, MA (US); Shyam Bharat, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 37 days.

(21) Appl. No.: 17/614,697

(22) PCT Filed: May 19, 2020

(86) PCT No.: PCT/EP2020/063878
§ 371 (c)(1),
(2) Date: Nov. 29, 2021

(87) PCT Pub. No.: WO2020/239514
PCT Pub. Date: Dec. 3, 2020

(65) Prior Publication Data
US 2022/0218302 A1  Jul. 14, 2022

Related U.S. Application Data

(60) Provisional application No. 62/885,013, filed on May 31, 2019.

(30) Foreign Application Priority Data

Jul. 31, 2019  (EP) ..................................... 19189347

(51) Int. Cl.
*A61B 34/20* (2016.01)
*A61B 8/00* (2006.01)
*A61B 8/08* (2006.01)

(52) U.S. Cl.
CPC .......... *A61B 8/0841* (2013.01); *A61B 8/4254* (2013.01); *A61B 8/483* (2013.01); *A61B 34/20* (2016.02)

(58) Field of Classification Search
CPC ..... A61B 8/0841; A61B 8/4254; A61B 8/483; A61B 34/20
See application file for complete search history.

(56) References Cited

U.S. PATENT DOCUMENTS

2007/0249934 A1* 10/2007 Aksit ............... G01R 33/34084
600/427
2013/0079628 A1  3/2013 Groszmann et al.
(Continued)

FOREIGN PATENT DOCUMENTS

JP  2017536903 A  12/2017
WO  2012095784 A1  7/2012
(Continued)

OTHER PUBLICATIONS

International Search Report and Written Opinion of PCT/EP2020/063878, dated Jul. 17, 2020.

*Primary Examiner* — Amal Aly Farag

(57) ABSTRACT

A controller (220) for determining a shape of an interventional medical device in an interventional medical procedure based on a location of the interventional medical device includes a memory (221) that stores instructions and a processor (222) that executes the instructions. The instructions cause a system (200) that includes the controller (220) to implement a process that includes obtaining (S320) the location of the interventional medical device (201) and obtaining (S330) imagery of a volume that includes the interventional medical device. The process also includes applying (S340), based on the location of the interventional medical device (201), image processing to the imagery to identify the interventional medical device (201) including the shape of the interventional medical device (201). The (Continued)

process further includes (S350) segmenting the interventional medical device (201) to obtain a segmented representation of the interventional medical device (201). The segmented representation of the interventional medical device (201) is overlaid (S360) on the imagery.

20 Claims, 8 Drawing Sheets

(56) References Cited

U.S. PATENT DOCUMENTS

| | | | |
|---|---|---|---|
| 2014/0094695 A1* | 4/2014 | Jain | A61B 8/481 |
| | | | 600/424 |
| 2014/0187947 A1* | 7/2014 | Hansegard | A61B 8/469 |
| | | | 600/443 |
| 2016/0317118 A1* | 11/2016 | Parthasarathy | G06T 7/70 |
| 2017/0116751 A1 | 4/2017 | Speidel | |
| 2017/0366756 A1* | 12/2017 | Robert | A61B 8/54 |

FOREIGN PATENT DOCUMENTS

| | | |
|---|---|---|
| WO | 2014155285 A1 | 10/2014 |
| WO | 2016009350 A1 | 1/2016 |
| WO | 2016088013 A1 | 6/2016 |
| WO | 2016092415 A1 | 6/2016 |
| WO | 2017218552 A1 | 12/2017 |
| WO | 2018178248 A1 | 10/2018 |

* cited by examiner

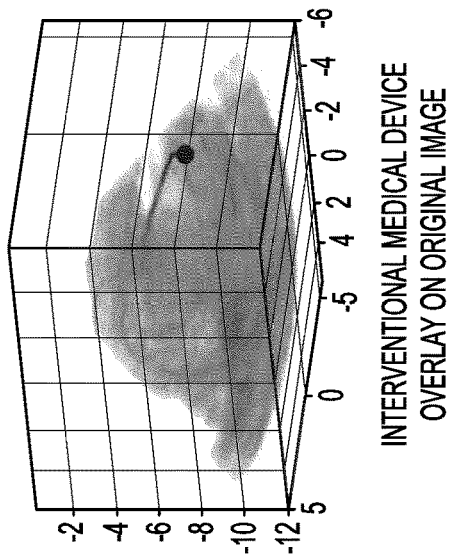
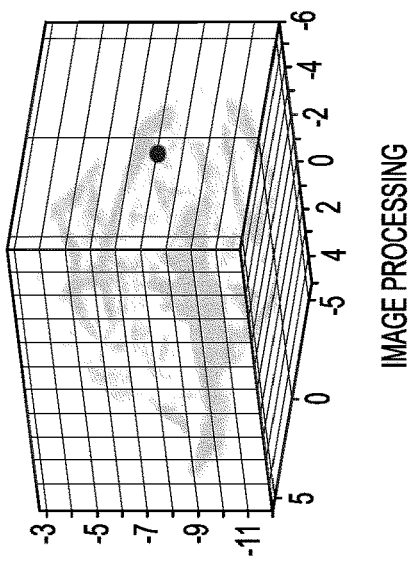
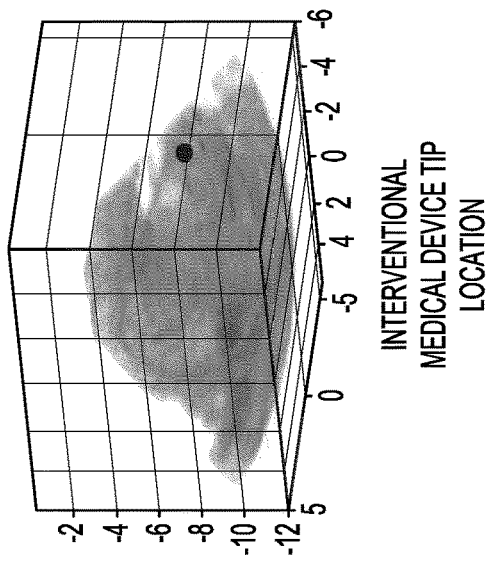
FIG.4C
FIG.4B
FIG.4A

PASSIVE-ULTRASOUND-SENSOR-BASED INITIALIZATION FOR IMAGE-BASED DEVICE SEGMENTATION

CROSS-REFERENCE TO PRIOR APPLICATIONS

This application is the U.S. National Phase application under 35 U.S.C. § 371 of International Application No. PCT/EP2020/063878, filed on May 19, 2020, which claims the benefit of U.S. Provisional Patent Application Ser. No. 62/855,013, filed May 31, 2019 and European Patent Application No. 19189347.8, filed on Jul. 31, 2019. These applications are hereby incorporated by reference herein.

BACKGROUND OF THE INVENTION

An ultrasound tracking technology estimates the position of a passive ultrasound sensor (e.g., PZT, PVDF, copolymer or other piezoelectric material) in the field of view (FOV) of a diagnostic ultrasound B-mode image by analyzing the signal received by the passive ultrasound sensor as imaging beams from an ultrasound probe sweep the field of view. A passive ultrasound sensor is an acoustic pressure sensor, and such a passive ultrasound sensor may be used to determine a location of an interventional medical device to which it is attached. Time-of-flight measurements provide the axial/radial distance of the passive ultrasound sensor from an imaging array of the ultrasound probe, while amplitude measurements and knowledge of the direct beam firing sequence provide the lateral/angular position of the passive ultrasound sensor.

FIG. 1 illustrates a known system for tracking an interventional medical device using a passive ultrasound sensor. In FIG. 1, an ultrasound probe 102 emits an imaging beam 103 that sweeps across a passive ultrasound sensor 104 on a tip of an interventional medical device 105. An image of tissue 107 is fed back by the ultrasound probe 102. A location of the passive ultrasound sensor 104 on the tip of the interventional medical device 105 is provided as a tip location 108 upon determination by a signal processing algorithm. The tip location 108 is overlaid on the image of tissue 107 as an overlay image 109. The image of tissue 107, the tip location 108, and the overlay image 109 are all displayed on a display 100.

The known technology for passive ultrasound sensors provides the location of the passive ultrasound sensor 104 but not the shape of the interventional medical device 105. In many clinical situations, such as for example cardiac and vascular interventions, it may be advantageous to determine the shape of the interventional medical device 105.

SUMMARY OF THE INVENTION

It is an object of the invention to at least partly provide this shape.

According to an aspect of the present disclosure, a controller for determining a shape of an interventional medical device in an interventional medical procedure based on a location of the interventional medical device includes a memory that stores instructions and a processor that executes the instructions. When executed by the processor, the instructions cause a system that includes the controller to implement a process that includes obtaining the location of the interventional medical device and obtaining imagery of a volume that includes the interventional medical device. The process implemented when the processor executes the instructions also includes applying, based on the location of a point on the interventional medical device, image processing to the imagery to identify the interventional medical device including the shape of the interventional medical device. The process implemented when the processor executes the instructions further includes segmenting the interventional medical device to obtain a segmented representation of the interventional medical device. The segmented representation of the interventional medical device is overlaid on the imagery.

According to another aspect of the present disclosure, a tangible non-transitory computer readable storage medium stores a computer program. When executed by a processor, the computer program causes a system that includes the tangible non-transitory computer readable storage medium to perform a process for determining a shape of an interventional medical device in an interventional medical procedure based on a location of the interventional medical device. The process performed when the processor executes the computer program from the tangible non-transitory computer readable storage medium includes obtaining the location of at least one point on the interventional medical device and obtaining imagery of a volume that includes the interventional medical device. The process performed when the computer program is executed by a processor also includes applying, based on the location of the interventional medical device, image processing to the imagery to identify the interventional medical device including the shape of the interventional medical device. The process performed when the computer program is executed by a processor further includes segmenting the interventional medical device to obtain a segmented representation of the interventional medical device. The segmented representation of the interventional medical device is overlaid on the imagery.

According to yet another aspect of the present disclosure, a system for determining a shape of an interventional medical device in an interventional medical procedure based on a location of a passive ultrasound sensor located using an ultrasound imaging probe includes an ultrasound imaging probe, a passive ultrasound sensor, and a controller. The ultrasound imaging probe emits beams during the interventional medical procedure. The passive ultrasound sensor is fixed to the interventional medical device during the interventional medical procedure. The controller includes a memory that stores instructions and a processor that executes the instructions. When executed by the processor, the instructions cause the system to implement a process that includes obtaining the location of the passive ultrasound sensor based on emission of a beam from the ultrasound imaging probe and obtaining imagery of a volume that includes the interventional medical device and the passive ultrasound sensor. The process implemented when the processor executes the instructions also includes applying, based on the location of the passive ultrasound sensor, image processing to the imagery to identify the interventional medical device including the shape of the interventional medical device and location of the interventional medical device. The process implemented when the processor executes the instructions further includes segmenting the interventional medical device to obtain a segmented representation of the interventional medical device. The segmented representation of the interventional medical device is overlaid on the imagery together with the location of the passive ultrasound sensor.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 4 illustrates a visualization progression for passive-ultrasound-sensor-based initialization for image-based device segmentation, in accordance with a representative embodiment, in accordance with a representative embodiment.

DETAILED DESCRIPTION OF THE EMBODIMENTS

Figure 1:
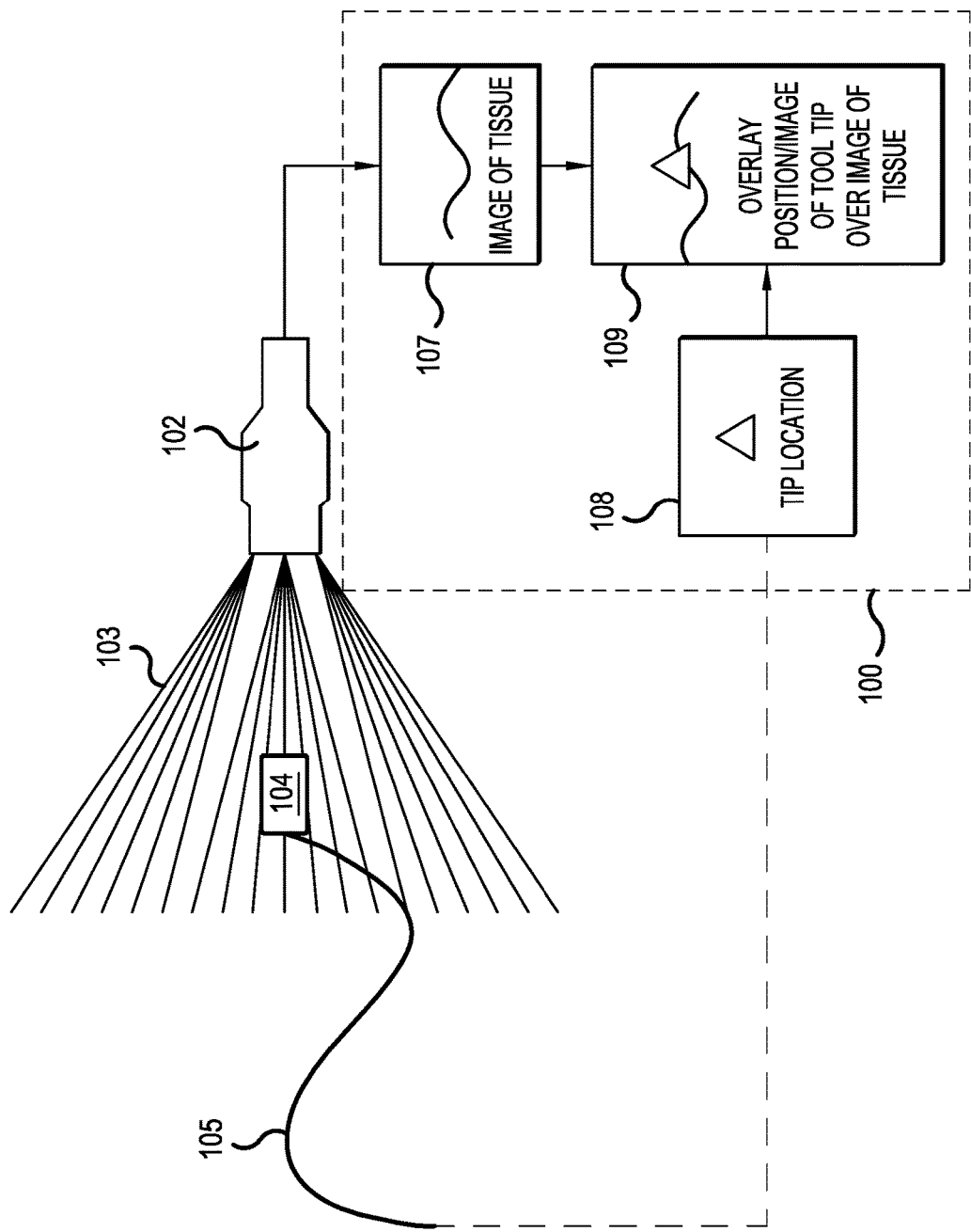
FIG. 1 illustrates a known system for tracking an interventional medical device using a passive ultrasound sensor.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, the shape of the interventional medical device (e.g., a wire) can be obtained readily using the location of the passive ultrasound sensor. The shape can be quantified using the system that identifies the location of the passive ultrasound sensor. The location of the passive ultrasound sensor can be used to initialize image processing algorithms that use, for example, spatial filtering or cross correlation with a known shape, to determine the shape of the device. Once the shape of the interventional medical device is determined, a mesh of the interventional medical device can be generated and overlaid to enhance visualization.

Figure 2:
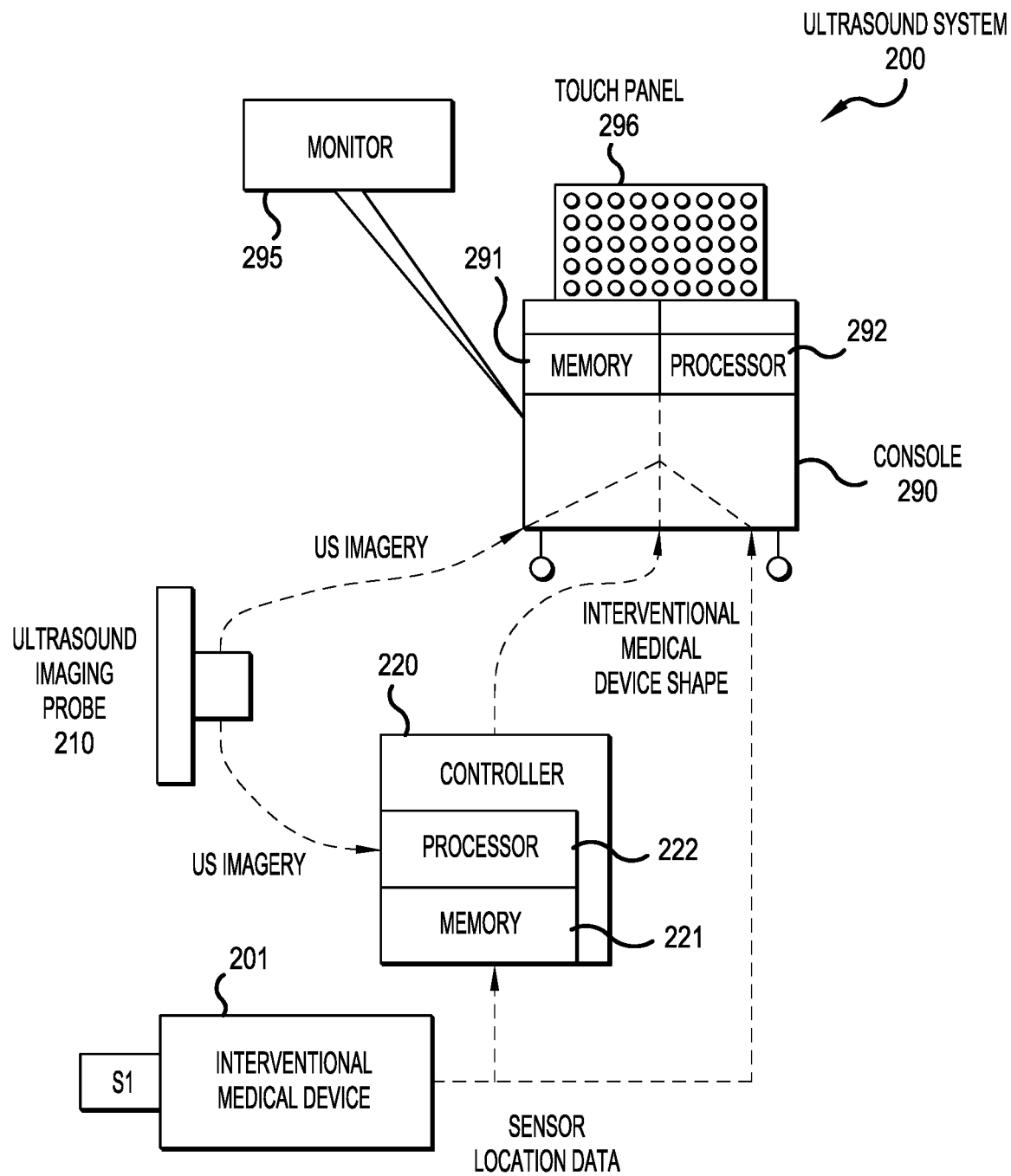
FIG. 2 illustrates a system for passive-ultrasound-sensor-based initialization for image-based device segmentation, in accordance with a representative embodiment.

FIG. 2 illustrates a system for passive-ultrasound-sensor-based initialization for image-based device segmentation, in accordance with a representative embodiment.

In FIG. 2, an ultrasound system 200 includes an ultrasound imaging probe 210, a controller 220, a console 290, an interventional medical device 201 and a passive ultrasound sensor S1. As a caveat, the ultrasound system 200 is representative of a system that includes a controller 220 used to obtain a location of an interventional medical device and imagery of a volume that include the interventional medical device. However, other types of location and imaging systems may be used to perform features described herein, and still fall within the spirit and scope of the present disclosure. Similarly, the ultrasound system 200 is representative of a system that includes a controller 220 for applying image processing to the imagery based on the location of the interventional medical device 201, and for segmenting the interventional medical device to obtain a segmented representation of the interventional medical device 201. However, other types of imaging systems may be used to perform these features described herein, and still fall within the spirit and scope of the present disclosure. Thus, a system as described herein does not have to be an ultrasound system.

The controller 220 includes a memory 221 that stores instructions and a processor 222 that executes the instructions. As another caveat, a controller 220 as described herein may be distributed among multiple devices that each include a combination of memory and processor to perform one or more characteristic functions attributed to the controller 220 herein.

The console 290 includes a memory 291 that stores instructions and a processor 292 that executes the instructions. The console 290 also includes a monitor 295 and a touch panel 296. The memory 291 and the processor 292 may be considered a sensor unit that determines the location of the passive ultrasound sensor S1 and provides the location of the passive ultrasound sensor S1 to the controller 220. Alternatively, another combination of a memory and a processor (not shown) may be used to receive the voltage readings from the passive ultrasound sensor S1 and the timing of beams from the ultrasound imaging probe 210 and determine the location of the passive ultrasound sensor S1 to provide to the controller 220.

Using the ultrasound system 200 or other embodiments consistent with the description herein, a shape of an interventional medical device 201 can be quantified by locating the tip of the interventional medical device 201 (or another location on the interventional medical device 201) using a passive ultrasound sensor S1. The tip of the interventional medical device 201 is located using the passive ultrasound sensor S1 in either a two-dimensional or a three-dimensional ultrasound space. Afterwards, image processing techniques, such as spatial filtering, are applied to the ultrasound image to enhance structures that are potentially identifiable as the body of the interventional medical device 201. The interventional medical device 201 may be segmented and overlaid on the image based on the most prominent device-like structures that appear near the known location of the passive ultrasound sensor S1.

A processor 222 or a processor 292 for a controller is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor 222 for a controller 220 is configured to execute software instructions to perform functions as described in the various embodiments herein. A processor 22 for a controller 220 may be a general-purpose processor or may be part of an application specific integrated circuit (ASIC). A processor 222 for a controller may also be a microprocessor, a microcomputer, a processor chip, a controller, a microcontroller, a digital signal processor (DSP), a state machine, or a programmable logic device. A processor 222 for a controller may also be a logical circuit, including a programmable gate array (PGA) such as a field programmable gate array (FPGA), or another type of circuit that includes discrete gate and/or transistor logic. A processor 222 for a controller may be a central processing unit (CPU), a graphics processing unit (GPU), or both. Additionally, any processor described herein may include multiple processors, parallel processors, or both. Multiple processors may be included in, or coupled to, a single device or multiple devices. A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each including a processor or processors. Many programs have instructions performed by multiple processors that may be within the same computing device or which may even be distributed across multiple computing devices.

Memories such as the memory 221 or the memory 291 described herein are tangible storage mediums that can store data and executable instructions and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted. "Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

For convenience, reference to features of the ultrasound system 200 will be used throughout the present disclosure in and for other embodiments for the sake of consistency. However, as noted above the ultrasound system 200 is only an example of a system that may perform the functions and functionality described herein.

Figure 3:
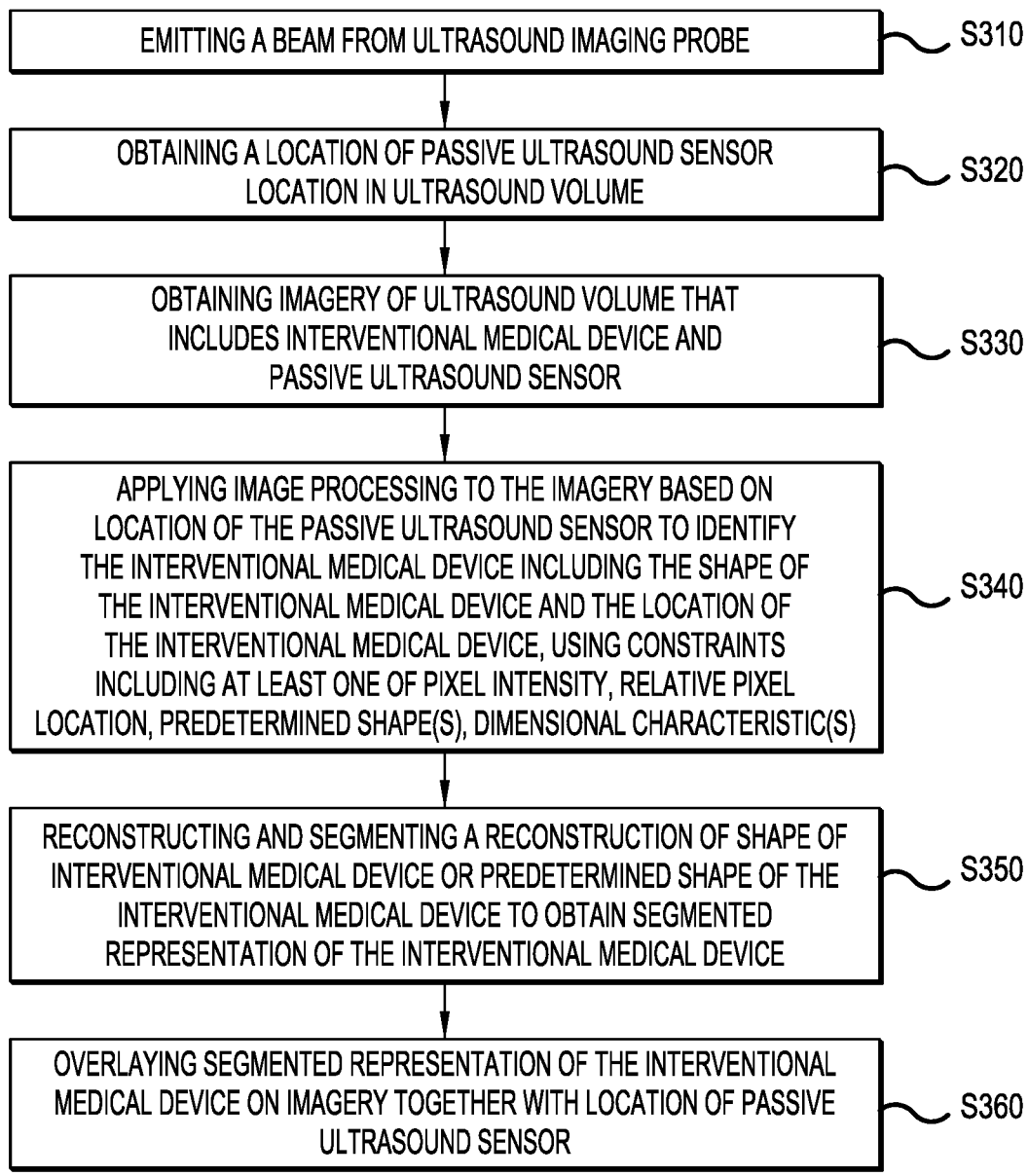
FIG. 3 illustrates a process for passive-ultrasound-sensor-based initialization for image-based device segmentation, in accordance with a representative embodiment.

FIG. 3 illustrates a process for passive-ultrasound-sensor-based initialization for image-based device segmentation, in accordance with a representative embodiment.

At S310, the process of FIG. 3 begins by emitting a beam from an ultrasound imaging probe. For example, the ultrasound imaging probe 210 in FIG. 2 may emit the beam as part of a sequence of beams at S310.

Next, at S320, the process of FIG. 3 proceeds to obtaining a location of a passive ultrasound sensor S1 location in an ultrasound volume. The location of the passive ultrasound sensor S1 may be determined in a predetermined three-dimensional coordinate system with an origin set for the ultrasound imagery. Registration may be performed to align the three-dimensional coordinate system for the ultrasound imagery with other three-dimensional coordinate systems, such as for the interventional medical device 201 including for imagery from the viewpoint of the interventional medical device when the interventional medical device 201 is an imaging device such as an endoscope. Registration may be performed by aligning landmarks in imagery in two different underlying coordinate systems in order to import one coordinate system to the other by image transformation. Registration may also be performed to align 2D or 3D ultrasound imagery to a 2D or projection imaging space, for example by identifying common landmarks in each imaging space or identifying the pose of the ultrasound transducer in another imaging space.

At S330, the process of FIG. 3 next includes obtaining imagery of the ultrasound volume that includes the interventional medical device 201 and the passive ultrasound sensor S1. The imagery may be ultrasound imagery resulting from the ultrasound beams emitted by the ultrasound imaging probe 210 during the interventional medical procedure.

At S340, the process of FIG. 3 includes applying image processing to the imagery based on the location of the passive ultrasound sensor S1 to identify the interventional medical device 201 including the shape of the interventional medical device 201 and the location of the interventional medical device 201, using constraints. The image processing at S340 may be applied based on a location of a point on the interventional medical device 201 or based on a location of at least one point on the interventional medical device 201. The constraints used at S340 may include one or more of characteristics of pixel intensity, of relative pixel location, of predetermined shape(s), and/or of dimensional characteristic(s). As an example, pixel intensity of pixels corresponding to locations of the interventional medical device 201 may be higher than for pixel intensity of pixels corresponding to anatomical features of the subject of the interventional medical procedure. As another example, the search may be limited to pixels within a predetermined range measured in distance, pixels or something else, from the pixels corresponding to the location of the passive ultrasound sensor S1. The image processing may involve filtering the pixels to eliminate pixels based on predetermined characteristics, so that the remaining elements of the original image better show the interventional medical device 201. That is, elements of the device shape (i.e., of the interventional medical device 201) remain after the filtering. The image processing therefore intentionally discards representations of shapes such as anatomical features, but not necessarily based on the shape insofar as the discarding may be based on the pixel intensity or pixel location and so on.

In other examples, the characteristics used for the image filtering may include a predetermined shape selected from, for example, a library of predetermined shapes corresponding to different interventional medical devices with different shapes. In another example, the characteristics used for the image filtering may include a dimensional characteristic of a predetermined shape, such as a minimum or maximum length, width, height, diameter, radius, cross-sectional area, curvature, and so on. For example, a wire as the interventional medical device 201 may have a very small cross-section, and the search for the wire may look for an end with an area or diameter less than a threshold corresponding to the very small cross-section.

At S350, the process of FIG. 3 next includes reconstructing and segmenting a reconstruction of a shape of an interventional medical device 201 or a predetermined shape of the interventional medical derive to obtain a segmented representation of the interventional medical device 201. The predetermined device shape may be used as a predetermined constraint so that the predetermined device shape is used as a candidate for the shape of the interventional medical device 201. The elements of the device shape (i.e., of the interventional medical device 201) remaining after filtering may be used for reconstructing the device shape. Segmentation is a representation of the surface of structures such as anatomical features and/or interventional medical devices such as the interventional medical device 201 and consists for example of a set of points in three-dimensional (3-D) coordinates on the surfaces of the structure, and triangular plane segments defined by connecting neighboring groups of three points, such that the entire structure is covered by a mesh of non-intersecting triangular planes. A three-dimensional model of the structure is obtained by segmenting. Segmenting as described herein for S350 and similar operations in other embodiments may involve performing segmentation on an interventional medical device 201, anatomy structures, and/or other structures present in a three-dimensional ultrasound volume.

At S360, the process of FIG. 3 includes overlaying the segmented representation of the interventional medical device 201 on imagery together with the location of the passive ultrasound sensor S1.

The process of FIG. 3 and the features of other embodiments herein can be used for many types of interventional procedures. For example, in structural heart repair, the use of the features herein can be used to check to ensure the correct shape/path during deployment of an interventional medical device 201. Additionally or alternatively, the use of the features herein can be used to detect whether the interventional medical device 201 has left a desired path during invasive procedures such as septal punctures. For example, a reference marker can be placed at the location of the target anatomy. As an additional or alternative use of the features described herein for structural heart repair, a shape of a mitral valve or other implant may be quantified in three dimensions during structural heart repair.

FIG. 4 illustrates a visualization progression for passive-ultrasound-sensor-based initialization for image-based device segmentation, in accordance with a representative embodiment, in accordance with a representative embodiment.

In visualization A, the progression of FIG. 4 shows an interventional medical device 201 tip location.

At visualization B, the progression of FIG. 4 shows the effects or results of image processing. In FIG. 4, the effect is much reduced detail of the overall imagery, but much greater detail of the interventional medical device 201.

At visualization C, the progression of FIG. 4 shows the interventional medical device 201 overlaid on the original image. That is, the interventional medical device 201 identified and highlighted in visualization B may be overlaid in visualization C. Of course, the visualization of the interventional medical device 201 from visualization B may be augmented such as by filling in missing pixels in order to entirely populate the full expected shape according to a model retrieved from a library of models. Therefore, the image processing used to reduce the detail of the overall imagery for visualization B may also include augmenting to enhance the detail of the interventional medical device.

In FIG. 4, the shape of the interventional medical device 201 is obtained from image processing that is initialized based on the location of the passive ultrasound sensor S1.

The tip or other location of the interventional medical device 201 is located in the 3D volume using tracking of the passive ultrasound sensor S1. Image processing techniques are applied to, in the embodiment of FIG. 4, make tube-like structures appear more clearly. The highest intensity tube-like structure near the location of the passive ultrasound sensor S1 may be assumed to be the body of the interventional medical device 201, which is then overlaid on the original image.

In an embodiment, a process that involves the progression of FIG. 4 may be used for an image processing algorithm applied in a three-dimensional volume to locate and enhance the visualization of the interventional medical device 201. The two-dimensional imaging plane from an ultrasound imaging probe 210 may be used to sweep the three-dimensional space that includes the interventional medical device 201. The resultant imagery may be analyzed subsequently to obtain a three-dimensional volumetric model of the space and/or the interventional medical device 201 in the space. The three-dimensional volumetric model of the space and/or the interventional medical device 201 may then be segmented. As an example, an initial two-dimensional plane may be set so that it includes a passive ultrasound sensor, and then the two-dimensional plane is incrementally rotated to roughly pivot around the passive ultrasound sensor. Two-dimensional image processing such as filtering and clustering may be performed on each frame in the rotational sweep to identify portions of the interventional medical device 201. The view of the interventional medical device 201 in each plane may be analyzed to determine which plane from the sweep provides the best display of the device, such as the longest section of the device, or shows the most distal portion near the passive ultrasound sensor. The segmentation of the interventional medical device is then displayed.

Figure 5:
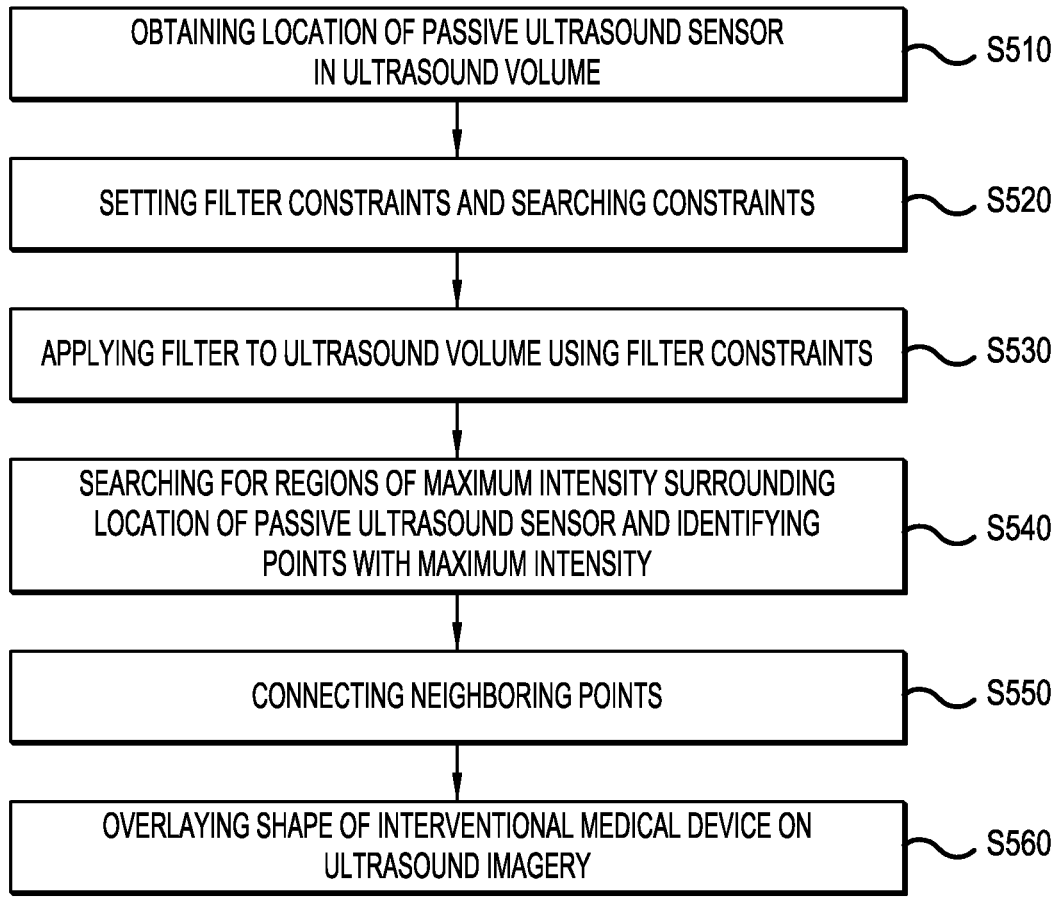
FIG. 5 illustrates another process for passive-ultrasound-sensor-based initialization for image-based device segmentation, in accordance with a representative embodiment.

FIG. 5 illustrates another process for passive-ultrasound-sensor-based initialization for image-based device segmentation, in accordance with a representative embodiment.

At S510, the process of FIG. 5 starts with obtaining a location of a passive ultrasound sensor S1 in an ultrasound volume.

At S520, the process of FIG. 5 next includes setting filter constraints and searching the constraints. That is, a search for the interventional medical device 201 in imagery may start at the location of the passive ultrasound sensor S1. A search for the constraints may be a search for regions in the imagery that satisfy predetermined constraints. A region that satisfied predetermined constraints may be within a specified radius or distance from the passive ultrasound sensor and may include characteristics such one or more pixels with a pixel intensity higher than a predetermined threshold. In an example, the predetermined constraints may be for a particular shape that is part of the shape of the interventional medical device 201, such as a corner or set of corners, one or more angles in the profile of the interventional medical device 201 that would appear in ultrasound imagery, and other types of constraints. The constraints may be predetermined constraints, and may vary based on the type of interventional medical device 201, the type of surgery, and characteristics of the subject of the interventional medical procedure including anatomical characteristics At S530, the process of FIG. 5 next moves to applying a filter to the ultrasound volume using the filter constraints. A process performed by a controller 220 or the ultrasound system 200 that includes the controller 220 may include filtering the imagery from an ultrasound imaging system to eliminate representations of a subject of the interventional medical procedure. For example, filtering may be performed to eliminate representations of tissue, bone and other anatomical features of the subject of the interventional medical procedure, since the object sought in the image processing is the interventional medical device 201.

At S540, the process of FIG. 5 includes searching for regions of maximum intensity surrounding the location of the passive ultrasound sensor and identifying points with the maximum intensity. The maximum intensity may be a pixel intensity above a predetermined threshold, or a relative intensity greater than a predetermined threshold of intensities of nearby pixels.

At S550, the process of FIG. 5 next includes connecting neighboring points. The neighboring points may be for pixels with intensities over a threshold and within a predetermined distance from the location of the passive ultrasound sensor S1.

At S560, the process of FIG. 5 ends with overlaying the shape of the interventional medical device 201 on the ultrasound imagery. The overlaid interventional medical device 201 is a representation of the interventional medical device 201, and may be superimposed on the ultrasound imagery, and highlighted such as by a highlighted outline.

The process of FIG. 5 and other embodiments herein can be used for many types of interventional procedures. For example, in peripheral vascular interventions the features herein can be used for monitoring shape of an interventional medical device 201 such as a wire during stenosis or occlusion crossings to detect buckling of the interventional medical device 201. Additionally or alternatively, the features herein can be used to detect progression of an interventional medical device 201 such as a wire with respect to the vessel to check if the interventional medical device 201 has exited the vessel wall.

Figure 6:
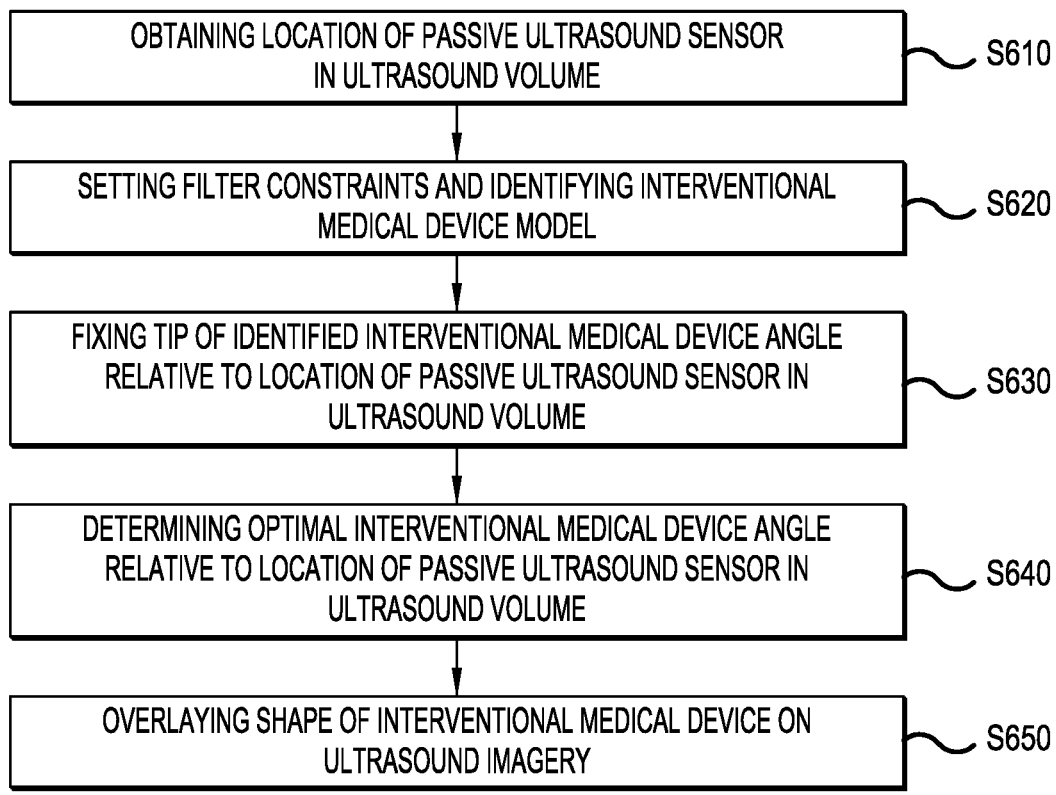
FIG. 6 illustrates another process for passive-ultrasound-sensor-based initialization for image-based device segmentation, in accordance with a representative embodiment.

FIG. 6 illustrates another process for passive-ultrasound-sensor-based initialization for image-based device segmentation, in accordance with a representative embodiment.

The process of FIG. 6 starts at S610 with obtaining a location of a passive ultrasound sensor in an ultrasound volume.

Next, at S620 the process of FIG. 6 includes setting filter constraints and identifying an interventional medical device 201 model. The filter constraints may be predetermined constraints or may be constraints that are dynamically set for each different interventional medical procedure. The filter constraints may be applied in order to identify regions that satisfy predetermined constraints, so that the image processing to be performed is only performed at the identified regions or at least starts at the identified regions.

At S630, the process of FIG. 6 next includes fixing a tip of an identified interventional medical device 201 model to a location of the passive ultrasound sensor in the ultrasound volume.

At S640, the process of FIG. 6 includes determining an interventional medical device 201 optimal angle relative to a location of the passive ultrasound sensor S1 in the ultrasound volume. The angle may be used to pose the interventional medical device 201 starting from the location ultrasound sensor S1 and aligned in the direction of the angle from the passive ultrasound sensor S1.

At S650, the process of FIG. 6 concludes with overlaying the shape of the interventional medical device 201 on the ultrasound surgery. For example, a mesh resulting from segmenting a shape of a predetermined structure as the interventional medical device 201 may be aligned based on the process at S640, and then placed so that the representation of the corner or other extremity of the interventional medical device 201 overlaps the representation of the passive ultrasound sensor S1 in or on the passive ultrasound imagery.

Figure 7:
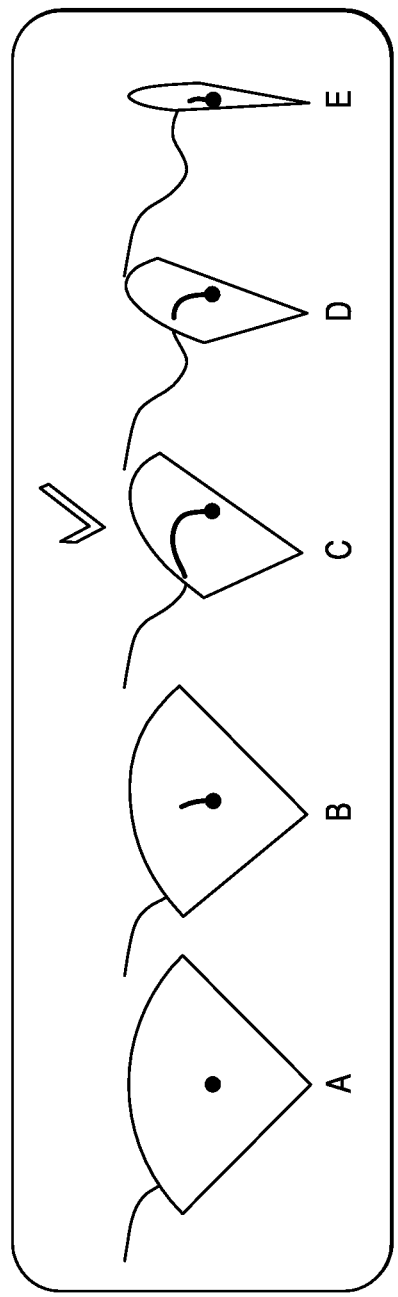
FIG. 7 illustrates a set of 2-dimensional or X-plane images used for optimizing a view for passive-ultrasound-sensor-based initialization for image-based device segmentation, in accordance with a representative embodiment.

FIG. 7 illustrates a set of 2-dimensional or X-plane images used for optimizing a view for passive-ultrasound-sensor-based initialization for image-based device segmentation, in accordance with a representative embodiment.

As shown in FIG. 7, five different 2-dimensional or X-plane images are labelled A, B, C, D and E, and each shows a view in which the interventional medical device 201 varies due to the differing viewpoints. The most complete view is that of 2-dimensional or X-plane image "C", which corresponds to the view with the greatest amount of detail of the interventional medical device 201.

In the embodiment of FIG. 7, imagery from two-dimensional or X-plane views can be viewed to see which provides the best detail of the interventional medical device 201. The imagery from FIG. 7 may be obtained before or after segmentation of the interventional medical device 201, and then used for example to identify or confirm the best placement, orientation and pose of the interventional medical device 201 on the underlying three-dimensional ultrasound volume. As an example consistent with an example described in the context of FIG. 4, an initial two-dimensional plane may be set so that it includes a passive ultrasound sensor, and then the two-dimensional plane is incrementally rotated to roughly pivot around the passive ultrasound sensor. In embodiments where location is determined by a mechanism other than passive ultrasound sensors, the location of a point on an interventional medical device 201 may still be used as the starting point of the sweep. Two-dimensional image processing such as filtering and clustering may be performed on each frame in the rotational sweep to identify portions of the interventional medical device 201. The view of the interventional medical device 201 in each plane can be analyzed to determine which plane from the sweep provides the best display of the device, such as the longest section of the device, or shows the most distal portion near the passive ultrasound sensor. The segmentation of the interventional medical device is then displayed.

Figure 8:
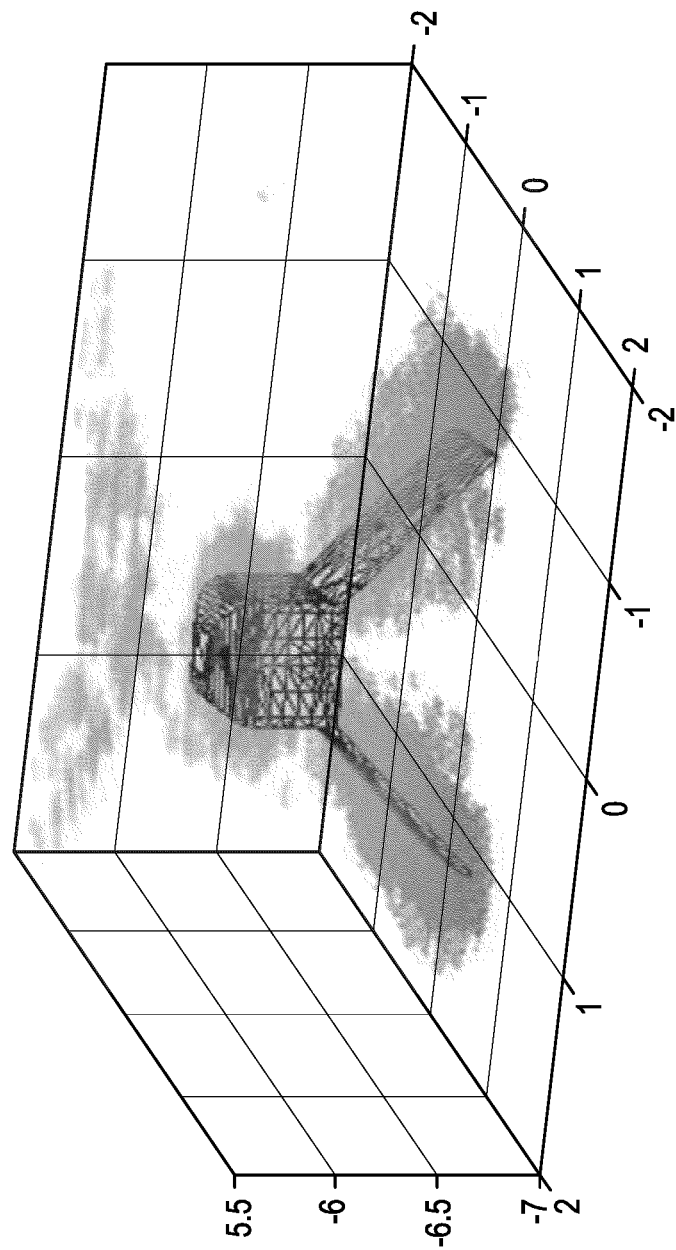
FIG. 8 illustrates a visualization of a mesh of an interventional medical device overlaid in an ultrasound volume in passive-ultrasound-sensor-based initialization for image-based device segmentation, in accordance with a representative embodiment.

FIG. 8 illustrates a visualization of a mesh of an interventional medical device 201 overlaid in an ultrasound volume in passive-ultrasound-sensor-based initialization for image-based device segmentation, in accordance with a representative embodiment.

In the embodiment of FIG. 8, the interventional medical device 201 may be a SHD device which is segmented into a mesh and overlaid in a 3-dimensional ultrasound volume. The shape of the interventional medical device 201 is known, and may be rigid, and can be fit to the ultrasound imagery of the 3-dimensional ultrasound volume. The location of the passive ultrasound sensor is used to initialize the search volume so as to identify the proper orientation, pose and overall placement of the interventional medical device 201 in FIG. 8.

As an example for the embodiment of FIG. 8, the interventional medical device 201 may be rigid, such as in the case of a transeptal puncture needle or mitral repair device. Image processing techniques can be used to search for the specific shape of the device in the region near the passive ultrasound sensor. The mesh of the known device can then be overlaid on the two-dimensional or three-dimensional ultrasound image as shown in FIG. 8. The overlaid mesh of the known device may be superimposed on the ultrasound imagery, and highlighted such as by color, brightness, or other visual characteristics to make the superimposed mesh distinctive in the combined image.

Accordingly, passive-ultrasound-sensor-based initialization for image-based device segmentation enables identification of an interventional medical device 201 in ultrasound imagery, and placement of a model of the interventional medical device 201 in or on the ultrasound imagery. The passive-ultrasound-sensor based initialization for image-based segmentation can be used in myriad ways such as to ensure that an interventional medical device 201 is being deployed in a correct pose and along a correct path, such as to detect irregular an path during an interventional medical procedure (e.g., septal puncture or chronic total occlusion crossing), and/or to quantify an interventional medical device 201 in three-dimensions during an interventional medical procedure.

Although passive-ultrasound-sensor-based initialization for image-based device segmentation has been described with reference to several exemplary embodiments, it is understood that the words that have been used are words of description and illustration, rather than words of limitation. Changes may be made within the purview of the appended claims, as presently stated and as amended, without departing from the scope and spirit of passive-ultrasound-sensor-based initialization for image-based device segmentation in its aspects. Although passive-ultrasound-sensor-based initialization for image-based device segmentation has been described with reference to particular means, materials and embodiments, passive-ultrasound-sensor-based initialization for image-based device segmentation is not intended to be limited to the particulars disclosed; rather passive-ultrasound-sensor-based initialization for image-based device segmentation extends to all functionally equivalent structures, methods, and uses such as are within the scope of the appended claims.

For example, examples above describe use of features herein for structural heart repair or peripheral vascular intervention. Other practical applications of the features herein may include detecting bending of an interventional medical device 201 such as a needle during a deep tissue biopsy. Other practical applications of the features herein may include providing a reliable in-body two-dimensional projection fiducial for registration between ultrasound and/to X-ray.

The following Examples are provided:

Example 1

A controller (220) for determining a shape of an interventional medical device (201) in an interventional medical procedure based on a location of the interventional medical device (201), comprising:
  a memory (221) that stores instructions, and
  a processor (222) that executes the instructions, wherein, when executed by the processor, the instructions cause a system that includes the controller (220) to implement a process that includes:
    obtaining (S320) the location of a point on the interventional medical device (201);
    obtaining (S330) imagery of a volume that includes the interventional medical device (201);
    applying (S340), based on the location of the interventional medical device, image processing to the imagery to identify the interventional medical device including the shape of the interventional medical device; and
    segmenting (S350) the interventional medical device to obtain a segmented representation of the interventional medical device, wherein the segmented representation of the interventional medical device is overlaid (S360) on the imagery.

Example 2

The controller (220) of Example 1, wherein the process implemented by the system further comprises:
obtaining (S320) a location of a passive ultrasound sensor based on emission of a beam from an ultrasound imaging probe, wherein the location of the interventional medical device corresponds to the location of the passive ultrasound sensor; and
starting (S340) a search for the interventional medical device in the imagery at the location of the passive ultrasound sensor and searching for regions in the imagery that satisfy predetermined constraints, to apply the image processing to the imagery,
wherein the segmented representation of the interventional medical device is overlaid on the imagery together with the location of the passive ultrasound sensor.

Example 3

The controller (220) of Example 2, wherein the process implemented by the system further comprises:
applying (S340) the predetermined constraints to the imagery to isolate regions in the imagery that potentially qualify as including a portion of the shape of the interventional medical device,
wherein the predetermined constraints include characteristics of pixel intensity, and pixel location relative to the location of the passive ultrasound sensor.

Example 4

The controller (220) of Example 2, wherein the process implemented by the system further comprises:
applying (S340) the predetermined constraints to the imagery to isolate regions in the imagery that potentially qualify as including a portion of the shape of the interventional medical device,
wherein the predetermined constraints include at least one predetermined shape used as a candidate for the shape of the interventional medical device.

Example 5

The controller (220) of Example 2, wherein the process implemented by the system further comprises:
applying (S340) the predetermined constraints to the imagery to isolate regions in the imagery that potentially qualify as including a portion of the shape of the interventional medical device,
wherein the predetermined constraints include at least one dimensional characteristic of a predetermined shape.

Example 6

The controller (220) of Example 1, wherein the process implemented by the system further comprises:
filtering (S340) the imagery to eliminate representations of a subject of the interventional medical procedure in which the interventional medical device is inserted, wherein elements of the shape of the interventional medical device remain in the imagery after the filtering, and
reconstructing (S350) the shape of the interventional medical device based on the elements of the shape of the interventional medical device remaining in the imagery after the filtering to obtain a reconstruction of the shape of the interventional medical device.

Example 7

The controller (220) of Example 6, wherein the segmenting is performed on the reconstruction of the shape of the interventional medical device, and the segmented representation of the interventional medical device comprises a segmented representation of the reconstruction of the shape of the interventional medical device.

Example 8

The controller (220) of Example 1, wherein the segmenting is performed on a predetermined shape based on the image processing, and the segmented representation of the interventional medical device comprises a segmented representation of the predetermined shape of the interventional medical device so that the segmented representation of the predetermined shape is overlaid on the imagery.

Example 9

A tangible non-transitory computer readable storage medium that stores a computer program, the computer program, when executed by a processor, causing a system that includes the tangible non-transitory computer readable storage medium to perform a process for determining a shape of an interventional medical device in an interventional medical procedure based on a location of the interventional medical device, the process performed when the processor (222) executes the computer program from the tangible non-transitory computer readable storage medium comprising:
obtaining (S320) the location of the interventional medical device;
obtaining (S330) imagery of a volume that includes the interventional medical device;
applying (S340), based on a location of at least one point on the interventional medical device, image processing to the imagery to identify the interventional medical device including the shape of the interventional medical device; and
segmenting (S350) the interventional medical device to obtain a segmented representation of the interventional medical device, wherein the segmented representation of the interventional medical device is overlaid (S360) on the imagery.

Example 10

The tangible non-transitory computer readable storage medium of Example 9, wherein the process implemented by the system further comprises:
starting (S340) a search for the interventional medical device in the imagery at the location of a passive ultrasound sensor and searching for regions in the imagery that satisfy predetermined constraints, to apply the image processing to the imagery.

Example 11

The tangible non-transitory computer readable storage medium of Example 10, wherein the process implemented by the system further comprises:
  obtaining (S320) a location of a passive ultrasound sensor based on emission of a beam from an ultrasound imaging probe, wherein the location of the interventional medical device corresponds to the location of the passive ultrasound sensor; and
  applying (S340) the predetermined constraints to the imagery to isolate regions in the imagery that potentially qualify as including a portion of the shape of the interventional medical device,
  wherein the predetermined constraints include characteristics of pixel intensity, and pixel location relative to the location of the passive ultrasound sensor,
  wherein the segmented representation of the interventional medical device is overlaid on the imagery together with the location of the passive ultrasound sensor.

Example 12

The tangible non-transitory computer readable storage medium of Example 10, wherein the process implemented by the system further comprises:
  applying (S340) the predetermined constraints to the imagery to isolate regions in the imagery that potentially qualify as including a portion of the shape of the interventional medical device,
  wherein the predetermined constraints include at least one predetermined shape used as a candidate for the shape of the interventional medical device.

Example 13

The tangible non-transitory computer readable storage medium of Example 10, wherein the process implemented by the system further comprises:
  applying (S340) the predetermined constraints to the imagery to isolate regions in the imagery that potentially qualify as including a portion of the shape of the interventional medical device,
  wherein the predetermined constraints include at least one dimensional characteristic of a predetermined shape.

Example 14

The tangible non-transitory computer readable storage medium of Example 9, wherein the process implemented by the system further comprises:
  filtering (S340) the imagery to eliminate representations of a subject of the interventional medical procedure in which the interventional medical device is inserted, wherein elements of the shape remain in the imagery after the filtering, and
  reconstructing (S350) the shape of the interventional medical device based on the elements of the shape of the interventional medical device remaining in the imagery after the filtering to obtain a reconstruction of the shape of the interventional medical device.

Example 15

The tangible non-transitory computer readable storage medium of Example 14,
  wherein the segmenting is performed on the reconstruction of the shape of the shape of the interventional medical device, and the segmented representation of the interventional medical device comprises a segmented representation of the reconstruction of the shape of the interventional medical device.

Example 16

The tangible non-transitory computer readable storage medium of Example 9,
  wherein the segmenting is performed on a predetermined shape based on the image processing, and the segmented representation of the interventional medical device comprises a segmented representation of the predetermined shape of the interventional medical device so that the segmented representation of the predetermined shape is overlaid on the imagery.

Example 17

A system (200) for determining a shape of an interventional medical device (201) in an interventional medical procedure based on a location of a passive ultrasound sensor (S1) located using an ultrasound imaging probe (210), comprising:
  an ultrasound imaging probe (210) that emits beams during the interventional medical procedure;
  a passive ultrasound sensor (S1) fixed to the interventional medical device (201) during the interventional medical procedure; and
  a controller (220) comprising a memory (221) that stores instructions and a processor (222) that executes the instructions, wherein, when executed by the processor (222), the instructions cause the system to implement a process that includes:
  obtaining (S320) the location of the passive ultrasound sensor based on emission of a beam from the ultrasound imaging probe;
  obtaining (S330) imagery of a volume that includes the interventional medical device and the passive ultrasound sensor;
  applying (S340), based on the location of the passive ultrasound sensor, image processing to the imagery to identify the interventional medical device including the shape of the interventional medical device and location of the interventional medical device; and
  segmenting (S350) the interventional medical device to obtain a segmented representation of the interventional medical device, wherein the segmented representation of the interventional medical device is overlaid (S360) on the imagery together with the location of the passive ultrasound sensor.

Example 18

The system of Example 17, further comprising:
  a sensor unit (291/292) that determines the location of the passive ultrasound sensor and provides the location of the passive ultrasound sensor to the controller (220); and
  a display (295) that displays the segmented representation of the interventional medical device based on the segmenting by the controller (220) and that displays the location of the passive ultrasound sensor determined by the sensor unit.

Example 19

The system of Example 17, wherein the process implemented by the system further comprises:
  starting (S340) a search for the interventional medical device in the imagery at the location of the passive ultrasound sensor and searching for regions in the imagery that satisfy predetermined constraints, to apply the image processing to the imagery.

Example 20

The system of Example 17, wherein the process implemented by the system further comprises:
  filtering (S340) the imagery to eliminate representations of a subject of the interventional medical procedure in which the interventional medical device is inserted, wherein elements of the shape remain in the imagery after the filtering, and
  reconstructing (S350) the shape based on the elements of the shape remaining in the imagery after the filtering to obtain a reconstruction of the shape of the interventional medical device.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A controller for determining a shape of an interventional medical device during an interventional medical procedure, the controller comprising:
  a memory configured to store instructions, and
  a processor configured to execute the instructions, and, when executed by the processor, the instructions cause the processor to:
  identify a location of a passive ultrasound sensor as a point on the interventional medical device in an ultrasound measurement space based on emission of ultrasound imaging beams from an ultrasound imaging probe during an interventional medical procedure, wherein the point is identified based on analysis of a signal received by the passive ultrasound sensor as the ultrasound imaging beams sweep the field of view of the ultrasound imaging probe, and wherein the location of the point corresponds to the location of the passive ultrasound sensor;
  obtaining, from the ultrasound imaging probe, ultrasound imagery of a volume that includes the interventional medical device;
  dynamically set filtering constraints to filter anatomical features from the ultrasound imagery based on the interventional medical procedure, wherein the filtering constraints include pixel intensity constraints;
  determine the shape of the interventional medical device by image processing of the obtained ultrasound imagery based on the identified location of the point on the interventional medical device, wherein the image processing comprises initializing imaging processing based on the identified location of the point and filtering of the ultrasound imagery based on the filtering constraints to enhance image features of the interventional medical device to be identifiable in the ultrasound imagery; and
  segmenting the interventional medical device to generate a segmented representation of the interventional medical device, wherein the segmented representation of the interventional medical device is overlaid on the ultrasound imagery.

2. The controller of claim 1, wherein, when executed by the processor, the instructions further cause the processor to: search for the interventional medical device in the ultrasound imagery at the location of the passive ultrasound sensor and for regions in the ultrasound imagery that satisfy predetermined constraints to apply the image processing to the ultrasound imagery.

3. The controller of claim 2, wherein, when executed by the processor, the instructions further cause the processor to: apply the predetermined constraints to the ultrasound imagery to isolate regions in the ultrasound imagery that potentially qualify as including a portion of the shape of the interventional medical device, wherein the predetermined constraints include characteristics of pixel intensity and pixel location relative to the location of the passive ultrasound sensor.

4. The controller of claim 2, wherein, when executed by the processor, the instructions further cause the processor to: apply the predetermined constraints to the ultrasound imagery to isolate regions in the ultrasound imagery that potentially qualify as including a portion of the shape of the interventional medical device, wherein the predetermined constraints include at least one predetermined shape used as a candidate for the shape of the interventional medical device.

5. The controller of claim 2, wherein, when executed by the processor, the instructions further cause the processor to: apply the predetermined constraints to the ultrasound imagery to isolate regions in the ultrasound imagery that potentially qualify as including a portion of the shape of the interventional medical device, wherein the predetermined constraints include at least one dimensional characteristic of a predetermined shape.

6. The controller of claim 1, wherein, when executed by the processor, the instructions further cause the processor to: further filter the ultrasound imagery to eliminate representations of a subject of the interventional medical procedure in which the interventional medical device is inserted, and reconstruct the shape of the interventional medical device based on the filtered ultrasound imagery to obtain a reconstruction of the shape of the interventional medical device.

7. The controller of claim 6, wherein, when executed by the processor, the instructions further cause the processor to perform the segmenting on the reconstruction of the shape of the interventional medical device, and the segmented representation of the interventional medical device comprises a segmented representation of the reconstruction of the shape of the interventional medical device.

8. The controller of claim 1, wherein, when executed by the processor, the instructions further cause the processor to perform the segmenting on a predetermined shape based on the image processing, and the segmented representation of the interventional medical device comprises a segmented representation of the predetermined shape of the interventional medical device so that the segmented representation of the predetermined shape is overlaid on the ultrasound imagery.

9. A tangible non-transitory computer readable storage medium that stores a computer program comprising instructions which, when executed by a processor, cause the processor to:
identify a location of a passive ultrasound sensor as a point on an interventional medical device in an ultrasound measurement space based on emission of ultrasound imaging beams from an ultrasound imaging probe during an interventional medical procedure, wherein the point is identified based on analysis of a signal received by the passive ultrasound sensor as the ultrasound imaging beams sweep the field of view of the ultrasound imaging probe, and wherein the location of the point corresponds to the location of the passive ultrasound sensor;
obtaining ultrasound imagery of a volume that includes the interventional medical device;
dynamically set filtering constraints to filter anatomical features from the ultrasound imagery based on the interventional medical procedure, wherein the filtering constraints include pixel intensity constraints;
determine the shape of the interventional medical device by image processing of the ultrasound imagery based on the identified location of the point on the interventional medical device, wherein the imaging processing comprises initializing imaging processing based on the identified location of the point and filtering of the ultrasound imagery based on the filtering constraints to enhance image features of the interventional medical device to be identifiable in the ultrasound imagery; and
segmenting the interventional medical device to generate a segmented representation of the interventional medical device, wherein the segmented representation of the interventional medical device is overlaid on the ultrasound imagery.

10. The tangible non-transitory computer readable storage medium of claim 9, wherein the instructions, when executed by the processor, further cause the processor to: search for the interventional medical device in the ultrasound imagery at the location of a passive ultrasound sensor and search for regions in the imagery that satisfy predetermined constraints, to apply the image processing to the ultrasound imagery.

11. The tangible non-transitory computer readable storage medium of claim 10, wherein the instructions, when executed by the processor, further cause the processor to: apply the predetermined constraints to the ultrasound imagery to isolate regions in the ultrasound imagery that potentially qualify as including a portion of the shape of the interventional medical device, wherein the predetermined constraints include characteristics of pixel intensity, and pixel location relative to the location of the passive ultrasound sensor.

12. The tangible non-transitory computer readable storage medium of claim 10, wherein the instructions, when executed by the processor, further cause the processor to: apply the predetermined constraints to the ultrasound imagery to isolate regions in the ultrasound imagery that potentially qualify as including a portion of the shape of the interventional medical device, wherein the predetermined constraints include at least one predetermined shape used as a candidate for the shape of the interventional medical device.

13. The tangible non-transitory computer readable storage medium of claim 10, wherein the instructions, when executed by the processor, further cause the processor to: apply the predetermined constraints to the ultrasound imagery to isolate regions in the ultrasound imagery that potentially qualify as including a portion of the shape of the interventional medical device, wherein the predetermined constraints include at least one-dimensional characteristic of a predetermined shape.

14. The tangible non-transitory computer readable storage medium of claim 9, wherein the instructions, when executed by the processor, further cause the processor to: further filter the ultrasound imagery to eliminate representations of a subject of the interventional medical procedure in which the interventional medical device is inserted, and reconstruct the shape of the interventional medical device based on the filtered ultrasound imagery to obtain a reconstruction of the shape of the interventional medical device.

15. The tangible non-transitory computer readable storage medium of claim 14, wherein the instructions, when executed by the processor, further cause the processor to perform the segmenting on the reconstruction of the shape of the shape of the interventional medical device, and the segmented representation of the interventional medical device comprises a segmented representation of the reconstruction of the shape of the interventional medical device.

16. The tangible non-transitory computer readable storage medium of claim 9, wherein the instructions, when executed by the processor, further cause the processor to perform the segmenting on a predetermined shape based on the image processing, and the segmented representation of the interventional medical device comprises a segmented representation of the predetermined shape of the interventional medical device so that the segmented representation of the predetermined shape is overlaid on the ultrasound imagery.

17. An ultrasound system for determining a shape of an interventional medical device in during an interventional medical procedure, the ultrasound system comprising:
- an ultrasound imaging probe configured to emit ultrasound imaging beams during the interventional medical procedure and generate ultrasound imagery of a volume that includes an interventional medical device;
- a passive ultrasound sensor fixed to the interventional medical device, the passive ultrasound sensor configured to receive the ultrasound beams emitted by the ultrasound imaging probe; and
- a controller comprising a processor configured to execute instructions stored in memory, and, when executed by the processor, the instructions cause the processor to:
  identify a location of the passive ultrasound sensor as a point on the interventional medical device in an ultrasound measurement space based on the ultrasound imaging beams emitted from the ultrasound imaging probe during an interventional medical procedure, wherein the point is identified based on analysis of a signal received by the passive ultrasound sensor as the ultrasound imaging beams sweep the field of view of the ultrasound imaging probe, and wherein the location of the interventional medical device corresponds to the location of the passive ultrasound sensor;
  obtain, from the ultrasound imaging probe, the ultrasound imagery of the volume that includes the interventional medical device;
  dynamically set filtering constraints to filter anatomical features from the ultrasound imagery based on the interventional medical procedure, wherein the filtering constraints include pixel intensity constraints;
  determine the shape of the interventional medical device by image processing of the ultrasound imagery based on the identified location of the point on the interventional medical device, wherein the imaging processing comprises initializing imaging processing based on the identified location of the point and filtering of the ultrasound imagery based on the filtering constraints to enhance image features of the interventional medical device to be identifiable in the ultrasound imagery; and
  segment the interventional medical device to generate a segmented representation of the shape of the interventional medical device, wherein the segmented representation of the interventional medical device is overlaid on the ultrasound imagery.

18. The ultrasound system of claim 17, wherein, when executed by the processor, the instructions further cause the processor to: determine the location of the passive ultrasound sensor and provide the location of the passive ultrasound sensor to the controller; and display the segmented representation of the interventional medical device.

19. The ultrasound system of claim 17, wherein, when executed by the processor, the instructions further cause the processor to: search for the interventional medical device in the ultrasound imagery at the location of the passive ultrasound sensor and searching for regions in the ultrasound imagery that satisfy predetermined constraints, to apply the image processing to the ultrasound imagery.

20. The ultrasound system of claim 17, wherein, when executed by the processor, the instructions further cause the processor to: filter the ultrasound imagery to eliminate representations of a subject of the interventional medical procedure in which the interventional medical device is inserted, wherein elements of the shape remain in the filtered ultrasound imagery, and reconstruct the shape based on the elements of the shape remaining in the filtered ultrasound imagery to obtain a reconstruction of the shape of the interventional medical device.

* * * * *